United States Patent [19]

Herzig et al.

[11] Patent Number: 5,214,077
[45] Date of Patent: May 25, 1993

[54] ORGANOSILICON COMPOUNDS CONTAINING (METH)ACRYLOXY GROUPS, THEIR PREPARATION AND USE

[75] Inventors: Christian Herzig, Taching; Bernard Deubzer; Inge Sigl, both of Burghausen, all of Fed. Rep. of Germany

[73] Assignee: Wacker-Chemie GmbH, Fed. Rep. of Germany

[21] Appl. No.: 867,654

[22] Filed: Apr. 13, 1992

[30] Foreign Application Priority Data

May 16, 1991 [DE] Fed. Rep. of Germany ........ 4116013

[51] Int. Cl.$^5$ .................. C08F 2/50; C08G 77/04; C08G 77/20; C07F 7/08
[52] U.S. Cl. ..................... 522/99; 522/172; 528/26; 528/31; 528/32; 556/440; 556/487; 556/488
[58] Field of Search ............ 522/99, 172; 528/26, 528/31, 32

[56] References Cited

U.S. PATENT DOCUMENTS

| | | | |
|---|---|---|---|
| 3,746,734 | 7/1973 | Berger et al. | 260/448.2 |
| 4,503,208 | 3/1985 | Lin et al. | 528/15 |
| 4,568,566 | 2/1986 | Tolentino | 528/26 |
| 4,575,546 | 3/1986 | Kemarczyk et al. | 522/26 |
| 4,675,346 | 6/1987 | Lin et al. | 522/99 |

FOREIGN PATENT DOCUMENTS

| | | |
|---|---|---|
| 0130731 | 1/1985 | European Pat. Off. |
| 0247501 | 12/1987 | European Pat. Off. |
| 0336633 | 10/1989 | European Pat. Off. |

*Primary Examiner*—Marion E. McCamish
*Assistant Examiner*—Susan Berman

[57] ABSTRACT

New organosilicon compounds are disclosed which contain (meth)acryloxy groups and consist of average units of the formula $$A_aR_bSiX_cO_{\frac{4-(a+b+c)}{2}}, \quad (I)$$

in which the radicals R are the same or different and represent monovalent, optionally halogenated hydrocarbon radicals having from 1 to 18 carbon atom(s) per radical, X is a radical which may be the same or different and represents a chlorine atom or a radical of the formula $-OR^1$, where $R^1$ represents an alkyl radical having from 1 to 8 carbon atom(s) per radical, which can be substituted by an ether oxygen atom, a is 0 or 1, with an average of from 0.01 to 1.0, b is 0, 1, 2 or 3, with an average of from 0.0 to 3.0, c is 0, 1, 2 or 3, with an average of from 0.0 to 3.0, the sum of $a+b+c \leq 4$, and is an average of from 1.5 to 4.0, and A is a radical of the formula $$HC[R^4(OR^3)_zOCCR^2=CH]_xH$$
$$\overset{\|}{\underset{O}{-C[R^4(OR^3)_zOCCR^2=CH]_yH}}$$

where x is 0 or 1 and y is 0 or 1, with the proviso that the sum of $x+y$ is 1, z is 1, 2, 3 or 4, $R^2$ represents a hydrogen atom or a methyl radical, $R^3$ represents a radical of the formula $-CH_2CH_2-$ or $-C(CH_3)HCH_2-$ and $R^4$ represents a linear or branched alkylene radical having from 1 to 6 carbon atom(s) per radical, with the proviso that the compounds contain at least one radical A per molecule.

9 Claims, No Drawings

ORGANOSILICON COMPOUNDS CONTAINING (METH)ACRYLOXY GROUPS, THEIR PREPARATION AND USE

The present invention relates to organosilicon compounds containing (meth)acryloxy groups and more particularly to a process for preparing organosilicon compounds containing (meth)acryloxy groups and their use as coatings.

BACKGROUND OF THE INVENTION

According to U.S. Pat. No. 4,405,208 (published Mar. 5, 1985, Samuel Q. S. Lin et al., Loctite Corp.), organopolysiloxanes containing acryloxy groups are obtained in a hydrosilylation reaction by reacting an organopolysiloxane containing Si-bonded hydrogen with propargyl (meth)acrylate. The propargyl alcohol employed in the preparation of the propargyl (meth)acrylate has a relatively high toxicity, and the esterification of propargyl alcohol with (meth)acrylic acid gives poor yields of propargyl (meth)acrylate.

The reaction of organopolysiloxanes containing Si-bonded hydrogen with beta-(allyloxy)ethyl methacrylate in the presence of a hydrosilylation catalyst is known from EP-A 130,731 (laid open Jan. 9, 1985, Samuel Q. S. Lin et al., Loctite Corp.). Organopolysiloxanes containing methacryloxy groups are obtained in this reaction, however, organopolysiloxanes containing acryloxy groups are not obtainable selectively by an analogous reaction, because the hydrosilylation occurs both on the acrylic and on the allyl radical.

Therefore, it is an object of the present invention to provide organosilicon compounds which contain (meth)acryloxy groups. Another object of the present invention is to provide a process for preparing organosilicon compounds having (meth)acryloxy groups with a high selectivity and in a simple process using readily available reactants. A further object of the present invention is to prepare organosilicon compounds containing (meth)acryloxy groups which may be used as coatings.

SUMMARY OF THE INVENTION

The foregoing objects and others which will become apparent from the following description are accomplished in accordance with this invention, generally speaking, by providing organosilicon compounds which contain (meth)acryloxy groups and contains average units of the formula $$A_a B_b SiX_c O_{\frac{4-(a+b+c)}{2}} \quad (I)$$

where the radicals R are the same or different and represent monovalent hydrocarbon radicals having from 1 to 18 carbon atom(s) per radical or halogenated monovalent hydrocarbon radicals having from 1 to 18 carbon atom(s) per radical, X represents the same or different radicals selected from chlorine atoms or a radical of the formula —OR$^1$, where R$^1$ represents an alkyl radical having from 1 to 8 carbon atom(s) per radical, which can be substituted by an ether oxygen atom, a is 0 or 1, with an average of from 0.01 to 1.0, b is 0, 1, 2 or 3, with an average of from 0.0 to 3.0, c is 0, 1, 2 or 3, with an average of from 0.0 to 3.0, the sum of $a+b+c \leq 4$, and is an average of from 1.5 to 4.0, and A is a radical of the formula

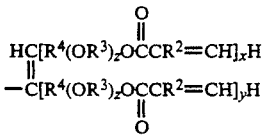

where x is 0 or 1 and y is 0 or 1, with the proviso that the sum of $x+y$ is 1, z represents 1, 2, 3 or 4, R$^2$ represents a hydrogen atom or a methyl radical, R$^3$ represents a radical of the formula —CH$_2$CH$_2$— or —C(CH$_3$)HCH$_2$—and R$^4$ represents a linear or branched alkylene radical having from 1 to 6 carbon atom(s) per radical, with the proviso that the compounds contain at least one radical A per molecule.

The invention also relates to a process for preparing the organosilicon compounds containing (meth)acryloxy groups, in which an organic compound (1) of the formula

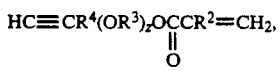

where R$^2$, R$^3$, R$^4$ and z are the same as above, is reacted with an organosilicon compound (2) having at least one Si-bonded hydrogen atom in its molecule in the presence of a catalyst (3) which promotes the addition of Si-bonded hydrogen onto an aliphatic multiple bond.

DESCRIPTION OF THE INVENTION

The organosilicon compounds of this invention are preferably silanes or organopolysiloxanes.

The organosilicon compounds of this invention preferably have an average molecular weight of from 246 to 1,000,000 g/mol, and more preferably from 300 to 50,000 g/mol, and preferably have a viscosity of 5 to 1,000,000 mm$^2 \cdot$s$^{-1}$ at 25° C. and more preferably from 20 to 100,000 mm$^2 \cdot$s$^{-1}$ at 25° C.

Examples of radicals R are alkyl radicals, such as the methyl, ethyl, n-propyl, iso-propyl, 1-n-butyl, 2-n-butyl, iso-butyl, tert-butyl, n-pentyl, iso-pentyl, neo-pentyl and tert-pentyl radicals; hexyl radicals such as the n-hexyl radical; heptyl radicals, such as the n-heptyl radical; octyl radicals, such as the n-octyl radical and iso-octyl radicals, such as the 2,2,4-trimethylpentyl radical; nonyl radicals, such as the n-nonyl radical; decyl radicals, such as the n-decyl radical; dodecyl radicals, such as the n-dodecyl radical; octadecyl radicals, such as the n-octadecyl radical; cycloalkyl radicals, such as the cyclopentyl, cyclohexyl and cycloheptyl radicals and methylcyclohexyl radicals; aryl radicals, such as the phenyl, naphthyl and anthryl and phenanthryl radical; alkaryl radicals, such as o-, m-and p-tolyl radicals, xylyl radicals and ethylphenyl radicals; and aralkyl radicals, such as the benzyl radical and the α- and β-phenylethyl radicals. The methyl radical is the preferred R radical.

Examples of halogenated radicals represented by R are haloalkyl radicals, such as the 3,3,3-trifluoro-n-propyl radical, the 2,2,2,2',2',2'-hexafluoroisopropyl radical and the heptafluoroisopropyl radical, and haloaryl radicals, such as the o-, m- and p-chlorophenyl radicals.

Examples of alkyl radicals represented by R$^1$ are methyl, ethyl, n- propyl, iso-propyl, 1-n-butyl, 2-n-butyl, iso-butyl and tert-butyl radicals. The methyl and ethyl radicals are the preferred $R^1$ radicals. Examples of alkyl radicals represented by $R^1$ which are substituted by an ether oxygen atom are the methoxyethyl and ethoxyethyl radicals.

The radical $R^2$ is preferably a hydrogen atom.

$R^3$ is preferably a radical of the formula —$CH_2CH_2$—.

Examples of alkylene radicals represented by $R^4$ are those of the formulas —$(CH_2)$—, —$CH(CH_3)$—, —$C(CH_3)_2$—, —$C(CH_3)(C_2H_5)$—, —$(CH_2)_2$— and —$(CH_2)_4$—, in which the radical of the formula —$(CH_2)$— is preferred.

Examples of radicals represented by A are those of the formulas

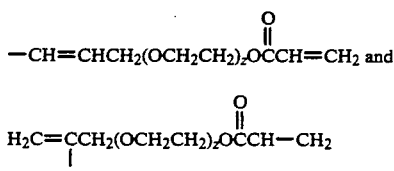

as well as

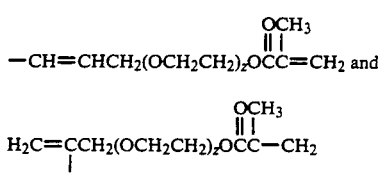

where z is the same as above and is preferably 1 or 2, and more preferably 1.

Preferred silanes containing (meth)acryloxy groups are those of the formula $$AR_dSiX_{3-d} \qquad (II)$$

where A, R and X are the same as above and d is 0, 1 or 2.

Preferred organopolysiloxanes containing (meth)acryloxy groups are those of the formula $$A_gR_{3-g}SiO(SiR_2O)_n(SiRAO)_mSiR_{3-g}A_g \qquad (III)$$

wherein A and R are the same as above, g is 0 or 1, n is 0 or an integer of from 1 to 1500 and m is 0 or an integer of from 1 to 100, with the proviso that the compounds contain at least one radical A per molecule.

Examples of organic compounds (1) which are employed in the process of this invention are those of the formulas

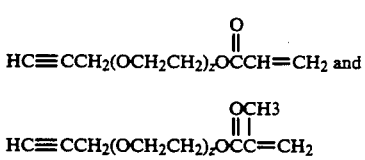

where z is the same as above and is preferably 1 or 2, and more preferably 1.

The organic compounds (1) are prepared by esterification of alkynoxyalkanols of the formula $HC\equiv CR^4(OR^3)_zOH$, where $R^3$, $R^4$ and z are the same as above, with (meth)acrylic acid. The alkynoxyalkanols are obtained by reacting alkynols with ethylene oxide or propylene oxide.

Catalysts which are employed are acids, such as p-toluenesulfonic acid, trifluoromethanesulfonic acid or sulfuric acid, and entraining agents which are used are hydrocarbons, such as cyclohexane, benzene or toluene. Stabilizer additions are advantageous; free radical stoppers, such as phenothiazine, methoxyphenol, butylated hydroxytoluene, copper or copper compounds, are preferably employed.

2-Propynoxyethanol is commercially available, for example, from BASF under the name Golpanol PME and has a considerably lower toxicity than propargyl alcohol.

As a result of the preparation, and also depending on the alkynoxyalkanol employed, z in the organic compound (1) can have on the average a value of less than 1 or between 1 and 2.

Silanes containing one Si-bonded hydrogen atom per molecule or organopolysiloxanes containing at least one Si-bonded hydrogen atom per molecule, of the formula $$H_eR_fSiO_{\frac{4-(e+f)}{2}} \qquad (IV)$$

where R is the same as above, e is 0 or 1, with an average of from 0.01 to 1.0, f is 0, 1, 2 or 3, with an average of from 0.0 to 3.0, and the sum of e+f is not greater than 3, are preferably employed as the organosilicon compound (2) containing at least one Si-bonded hydrogen atom per molecule.

The organopolysiloxanes containing at least one Si-bonded hydrogen atom preferably contain at least 0.04% by weight, and more preferably from 0.1 to 1.6% by weight, of Si-bonded hydrogen, and their average viscosity is preferably 2 to 20,000 $mm^2 \cdot s^{-1}$ at 25° C., more preferably from 2 to 2000 $mm^2 \cdot s^{-1}$ at 25° C., and especially from 2 to 200 $mm^2 \cdot s^{-1}$ at 25° C.

Silanes containing one Si-bonded hydrogen atom per molecule which are preferably used are those of the formula $$HR_dSiX_{3-d} \qquad (V)$$

where X is preferably $OR^1$ and R, $R^1$ and d are the same as above.

Organopolysiloxanes containing at least one Si-bonded hydrogen atom per molecule which are preferably used are those of the formula $$H_hR_{3-h}SiO(SiR_2O)_o(SiRHO)_pSiR_{3-h}H_h \qquad (VI)$$

where R is the same as above, h is 0 or 1, o is 0 or an integer of from 1 to 1500 and p is 0 or an integer of from 1 to 100.

A preferred example of silanes of formula (V) is triethoxysilane. Preferred examples of organopolysiloxanes of formula (VI) are copolymers of dimethylhydridosiloxane and dimethylsiloxane units, copolymers of dimethylhydridosiloxane, dimethylsiloxane and methylhydridosiloxane units, copolymers of trimethylsiloxane and methylhydridosiloxane units and copolymers of trimethylsiloxane, dimethylsiloxane and methylhydridosiloxane units.

Processes for the preparation of organopolysiloxanes containing at least one Si-bonded hydrogen atom per molecule, including those of the preferred type, are generally known.

The organic compound (1) is preferably employed in the process of this invention in amounts such that from 1 to 2 mol, preferably 1.05 to 1.20 mol, of organic compound (1) are present per gram atom of Si-bonded hydrogen in the organosilicon compound (2).

If the organosilicon compound (2) containing Si-bonded hydrogen atoms which is employed is easier to remove by distillation than the organic compound (1) employed, the organic compound (1) can be employed in amounts of less than 1 mol, to a maximum of 0.8 mol, per gram atom of Si-bonded hydrogen in the organosilicon compound (2).

The same catalysts which have been or could have been employed heretofore to promote the addition of Si-bonded hydrogen onto an aliphatic multiple bond can also be employed as the catalysts (3) to promote the addition of Si-bonded hydrogen onto an aliphatic multiple bond in the process of this invention. The catalysts (3) are preferably a metal from the group of the platinum metals or a compound or a complex from the group of the platinum metals. Examples of such catalysts are metallic and finely divided platinum, which can be supported on inert carriers, such as silicon dioxide, aluminum oxide or active charcoal, compounds or complexes of platinum, such as platinum halides, for example $PtCl_4$, $H_2PtCl_6 \cdot 6H_2O$, $Na_2PtCl_4 \cdot 4H_2O$, platinum-olefin complexes, platinum-alcohol complexes, platinum-alcoholate complexes, platinum-ether complexes, platinum-aldehyde complexes, platinum-ketone complexes, including reaction products of $H_2PtCl_6 \cdot 6H_2O$ and cyclohexanone, platinum-vinylsiloxane complexes, such as platinum-1,3-divinyl 1,1,3,3-tetramethyldisiloxane complexes with or without a detectable amount of inorganically bonded halogen, bis(gamma-picoline)platinum dichloride, trimethylenedipyridine-platinum dichloride, dicyclopentadiene-platinum dichloride, dimethyl sulfoxideethylene-platinum(II) dichloride, cyclooctadiene-platinum dichloride, norbornadiene-platinum dichloride, gamma-picoline-platinum dichloride and cyclopentadiene-platinum dichloride, and reaction products of platinum tetrachloride with olefin and primary amine or secondary amine or primary and secondary amines according to U.S. Pat. No. 4,292,434, such as the reaction products of platinum tetrachloride dissolved in 1-octene with sec-butylamine, or ammonium-platinum complexes according to EP-B 110,370.

The catalyst (3) is preferably employed in amounts of from 2 to 200 ppm by weight (parts by weight per million parts by weight), preferably in amounts of from 5 to 50 ppm by weight, calculated as elemental platinum and based on the total weight of organic compound (1) and organosilicon compound (2).

The process of this invention is preferably carried out at the pressure of the surrounding atmosphere, that is to say, for example, under 1020 hPa (absolute), but it can also be carried out under higher or lower pressures. The process of this invention is preferably carried out at a temperature of from 80° C. to 150° C., and more preferably from 110° C. to 125° C.

Inert, organic solvents can additionally be used in the process of this invention, although the additional use of inert, organic solvents is not preferred. Examples of inert, organic solvents are toluene, xylene, octane isomers and butyl acetate.

If excess organic compound (1) and inert organic solvent are used, they are preferably removed by distillation from the organosilicon compounds which contain alkenyl groups prepared by the process of this invention.

The silanes which contain (meth)acryloxy groups prepared by the process of this invention can be converted into organopolysiloxanes containing (meth)acryloxy groups in a manner which is known per se by, for example, mixed hydrolysis with chloro- or alkoxysilanes and/or by condensation with organopolysiloxanes which are capable of condensation.

The chloro- or alkoxysilanes which are preferably employed are those of the formula $$R_iSiX_{4-i}$$

where R and X are the same as above, and i is 0, 1, 2 or 3.

The organopolysiloxanes which are capable of condensation and are preferably employed are those of the formula $$HOR_2SiO(SiR_2O)_qH$$

where R is the same as above and q is an integer having a value of at least 1, or linear organopolysiloxanes which are capable of condensation and are obtained in a manner which is known per se from cyclic organopolysiloxanes of the formula $$(SiR_2O)_r$$

where R is the same as above, and r represents an integer having a value of from 3 to 10, by condensation and/or equilibration.

The organopolysiloxanes prepared by the process of this invention which contain (meth)acryloxy groups can be equilibrated with organopolysiloxanes (4) selected from the group consisting of linear organopolysiloxanes containing terminal triorganosiloxy groups, linear organopolysiloxanes containing terminal hydroxyl groups, cyclic organopolysiloxanes and copolymers of diorganosiloxane and monoorganosiloxane units.

Linear organopolysiloxanes which contain terminal triorganosiloxy groups and which are preferably employed are those of the formula $$R_3SiO(SiR_2O)_rSiR_3$$

where R is the same as above and r is 0 or an integer having a value of from 1 to 1500, linear organopolysiloxanes which contain terminal hydroxyl groups and are preferably employed are those of the formula $$HO(SiR_2O)_sH$$

where R is the same as above and s is an integer having a value of from 1 to 1500, cyclic organopolysiloxanes which are preferably employed are those of the formula $$(R_2SiO)_t$$

where R is the same as above and t is an integer of from 3 to 12, and copolymers which are preferably employed are those having units of the formulas $R_2SiO$ and $RSiO_{3/2}$ where R is the same as above.

The proportions of the organopolysiloxanes (4) and organopolysiloxanes containing (meth)acryloxy groups employed in the equilibration which is carried out, if appropriate, are determined merely by the desired content of (meth)acrylic groups in the organopolysiloxanes formed during the equilibration, and by the average chain length desired.

Acid catalysts which promote the equilibration are preferably employed in the equilibration which is carried out, if appropriate. Examples of such catalysts are sulfuric acid, phosphoric acid, trifluoromethanoic acid and phosphorus nitride chlorides, and acid catalysts which are solid under the reaction conditions, such as acid-activated bleaching earth, acid zeolites, sulfonated carbon and sulfonated styrene-divinylbenzene copolymers. Phosphonitrile chlorides are preferred. Phosphonitrile chlorides are preferably used in amounts of from 5 to 1000 ppm (parts per million) by weight, and more preferably from 50 to 200 ppm by weight, based on the total weight of organosilicon compounds employed. Although it is possible to use basic equilibration catalysts, these are not preferred.

The equilibration which is carried out, if appropriate, is preferably carried out at 80° C. to 150° C. under the pressure of the surrounding atmosphere, for example, under 1020 hPa (absolute). If desired, however, higher or lower pressures can also be used. The equilibration is preferably carried out in from 5 to 20% by weight, based on the total weight of the particular organosilicon compounds employed and water-immiscible solvent, such as toluene.

Before the mixture obtained from the equilibration is further processed, the catalyst can be rendered inactive.

The process of this invention can be carried out batchwise, semicontinuously or completely continuously.

The invention further relates to compositions which can be crosslinked by irradiation with light and contain (A) organopolysiloxanes containing (meth)acryloxy groups of this invention and (B) a photosensitizer.

The compositions which can be crosslinked by irradiation with light are used in preparing coatings.

The organopolysiloxanes of this invention which contain (meth)acryloxy groups are preferably crosslinked by ultraviolet light, such light having wavelengths preferably in the range of from 200 to 400 nm. The ultraviolet light can be generated, for example, in xenon or low-, medium- or high-pressure mercury lamps. Light having a wavelength of 400 to 600 nm, that is to say so called "halogen light", is also suitable for crosslinking.

Suitable photosensitizers are optionally substituted acetophenones, propiophenones, benzophenones, anthraquinones, benzils, carbazoles, xanthones, thioxanthones, fluorenes, fluorenones, benzoins, naphthalenesulfonic acids and benzaldehydes and cinnamic acids.

Examples of these are fluorenone, fluorene and carbazole; acetophenone; substituted acetophenones, such as 3-methylacetophenone, 2,2'-dimethoxy-2-phenylacetophenone, 4-methylacetophenone, 3-bromoacetophenone, 4-allylacetophenone, p-diacetylbenzene and p-tert-butyltrichloroacetophenone; propiophenone; substituted propiophenones, such as 1-[4-(methylthio)phenyl]-2-morpholinepropan-1-one; benzophenone; substituted benzophenones, such as Michler's ketone, 3-methoxybenzophenone, 4,4'-dimethylamino benzophenone, 4-methylbenzophenone,4-chlorobenzophenone, 4,4'-dimethoxybenzophenone and 4-chloro-4'-benzylbenzophenone; xanthone; substituted xanthones, such as 3-chloroxanthone, 3,9-dichloroxanthone and 3-chloro-8-nonylxanthone; thioxanthone; substituted thioxanthones, such as isopropenylthioxanthone; anthraquinone; substituted anthraquinones, such as chloroanthraquinone and anthraquinone-1,5-disulfonic acid disodium salt; benzoin; substituted benzoins, such as benzoin methyl ether; benzil; 2-naphthalenesulfonyl chloride; benzaldehyde; and cinnamic acid.

Photosensitizers are preferably employed in the compositions of this invention in amounts of from 0.01 to 10% by weight, and more preferably from 0.5 to 5% by weight, based on the total weight of the organopolysiloxanes to be crosslinked.

The coatings of this invention can be applied to surfaces, such as, for example, paper, wood, cork, films of plastic, such as polyethylene or polypropylene films, ceramic objects, glass, including glass fibers, metals, pasteboards, including those of asbestos, and woven and non-woven cloth of naturally occurring or synthetic organic fibers.

The compositions of this invention which can be crosslinked by irradiation with light can be applied to any desired surface to be coated in any desired manner which is suitable and widely known for preparing coatings from liquid substances, such as, for example by dipping, brushing, pouring, spraying, rolling on, printing, for example by means of an offset gravure coating devise, or knife or doctor coating.

Preparation of 2-propargyloxyethyl acrylate

About 540 g of 2-propynoxyethanol (commercially available under the tradename "Golpanol PME" from BASF, C≡C equivalent weight: 108) are esterified azeotropically with 540 g (7.5 mol) of acrylic acid with the addition of 500 ml of toluene, 2.5 g of phenothiazine, 2 g of CuCl and 5 g of concentrated H$_2$SO$_4$. About 120 ml of aqueous phase which, according to acid titration, contains 24.5 g of acrylic acid are separated off in the course of 4 hours at an increasing bottom temperature (110°–125° C.). Excess acrylic acid is largely neutralized by NaHCO$_3$ and washed with a total of 400 ml of H$_2$O. The toluene is distilled off in vacuo, followed by the acrylic ester itself, with the addition of 1 g of phenothiazine, under 2 hPa (absolute). About 692 g (85% of theory) of the slightly yellowish acrylate having a triple bond equivalent weight of 170 are obtained. It can be seen from the IH-NMR spectrum that the distillate also contains, in addition to 2-propargyloxyethyl acrylate, acrylates having a higher degree of ethoxylation and, corresponding to the 2-propynoxyethanol employed, having the average formula

where x=1.2. The alkyne proton is detachable as a typical triplet at 2.52 ppm (x=1) and 2.49 ppm (x=2.)

EXAMPLE 1

About 3 mg of platinum in the form of a solution of platinum tetrachloride in 1-octene are added to 170 g (1.00 equivalent of C≡C) of 2-propargyloxyethyl acrylate, the preparation of which is described above, and the mixture is heated to 115° C. under a nitrogen atmosphere. About 170 g (1.03 mol) of hydridotriethoxysilane are metered in over a period of 1.5 hours and the reaction mixture is kept at the same temperature for an additional hour. Volumetric determination of hydrogen liberated with potassium hydroxide shows a conversion of more than 98%, based on the triple bond employed. Excess hydridotriethoxysilane is removed by distillation at 100° C. under 2 hPa (absolute). The addition product of the starting components in the form of the 1-silyl and 2-silyl isomers is obtained in a quantitative yield (333 g) as a yellowish, readily mobile liquid having a viscosity of 7.9 mm$^2\cdot$s$^{-1}$ at 25° C. $^1$H-NMR spectrum (CDCl$_3$): 1-silyl isomer (48%): δ=5.72 ppm (dtr, a), δ=6.44 ppm (dtr, b).

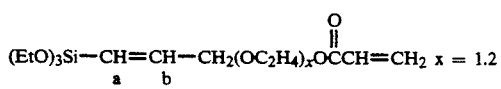

2-silyl isomer (52%): δ=5.77 ppm (dtr, a') δ=5.99 ppm (dtr, b')

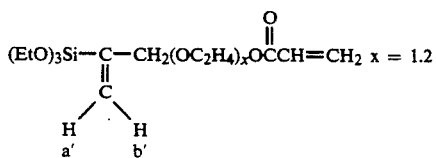

No SiCH$_2$CH$_2$CO$_2$ grouping is detected (detection limit about 1 mol %).

EXAMPLE 2

In each case 120 mg of methoxyphenol and phenothiazine are added to 187 g (1.1 equivalents of C≡C) of 2-propargyloxyethyl acrylate, prepared above. About 4 mg of platinum are then added in the form of a solution of platinum tetrachloride in 1-octene and the mixture is heated to 115° C. A total of 455 g of an α,w-dihydridodimethylpolysiloxane (1.0 equivalent of SiH) is then added dropwise over a period of about 2 hours. SiH analysis by volumetric determination of hydrogen liberated under alkaline conditions shows a conversion of more than 97% after an additional hour. A yellowish oil having an iodine number (number which indicates how many g of iodine are bonded by 100 g of substance) of 82 and a viscodensity of 21 mm$^2\cdot$s$^{-1}$ at 25° C. is obtained. Accoridng to the $^1$H-NMR spectrum (CDCl$_3$), the dimethylpolysiloxane chain has the isomeric end groups

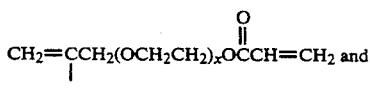

in a ratio of 33:67, where x is an average of 1.2. The geminal protons —C=CH2 of the first isomer have signals at 5.55 ppm and 5.80 ppm, and the two trans-protons of the second isomer are to be found in the region of 5.90 ppm and 6.15 ppm with I(trans) coupling of 19 Hz in the $^1$H-NMR spectrum.

EXAMPLE 3

The procedure of Example 2 is repeated, except that a total of 690 g of a copolymer of dimethylsiloxane, methylhydridosiloxane and trimethylsiloxane units which contains 0.145% by weight of Si-bonded hydrogen is added dropwise instead of the 455 g of the α,w-dihydridodimethylpolysiloxane. After a reaction time of an additional 4 hours, a conversion of about 97% is reached. The reaction mixture is cooled and filtered, and 860 g of a yellow oil having a viscosity of 130 mm$^2\cdot$s$^{-1}$ at 25° C. and an iodine number of 58 are obtained. The signals of the olefinic protons in the $^1$H-NMR spectrum result in an isomer ratio of 1-silyl product:2-silyl product of about 55:45.

EXAMPLE 4

About 100 g of the product from Example 2 are equilibrated with 800 g of α,w-dihydroxydimethylpolysiloxane having a viscosity of 20,000 mm$^2\cdot$s$^{-1}$, with the addition of 100 ppm of phosphonitrile chloride, at 100° C. for one hour. The catalyst is deactivated by stirring with 9 g of MgO. The reaction mixture is filtered and volatile constituents are removed by distillation at 100° C. under 2 hPa (absolute). The clear, almost colorless polymer has a viscosity of 610 mm$^2\cdot$s$^{-1}$ at 25° C. and shows a uniform peak for monomodal molecular weight distribution in the gel permeation chromatography spectrum. For better storage stability, the polymer can be inhibited with 100 ppm of methoxyphenol.

EXAMPLE 5

About 40 mg of 4-methoxyphenol and 14 mg of platinum in the form of a solution of platinum tetrachloride in 1-octene are added to 357 g (2.1 equivalents of C=C) of 2-propargyloxyethyl acrylate, prepared above. A total of 230 g (2.0 mol) of methyldichlorosilane is added dropwise at 115° C. under a nitrogen atmosphere over a period of about 3 hours. The reaction ceased after an additional 2 hours. After removal of the volatile constituents in vacuo under 5 hPa (absolute), 585 g of an addition product of the starting components, which contains about 3% by weight of the starting components, are obtained in the form of the 1-silyl and 2-silyl isomers. The product has an acid number of 375. $^1$H-NMR spectrum (CDCl$_3$): 1-silyl isomer (21%): δ=5.86 ppm (dtr, a), δ=6.53 ppm (dtr, b).

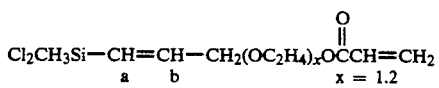

2-silyl isomer (79%): δ=5.92 ppm (dtr, a'). δ=6.06 ppm (dtr, b').

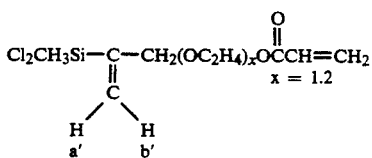

EXAMPLE 6

The product from Example 2 having an acrylate equivalent weight of about 600 g/acrylic double bond is mixed with 3% by 30 weight of the photosensitizer having the tradename Darocur ® 1173 (commercially available from Merck) and the mixture is applied as a coating at a thickness of 500 μ to a polyethylene film. The polymer is cross-linked within 2 seconds by irradiation with two medium-pressure mercury lamps having an output of 80 watts/cm luminous length at a distance of 10 cm. The surface of the coating is free from tackiness.

What is claimed is:

1. An organosilicon compound which contains (meth)acryloxy groups and consists of average units of the formula

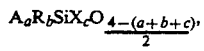 (I)

where R is a radical selected from the group consisting of monovalent hydrocarbon radicals having from 1 to 18 carbon atom(s) per radical and monovalent halogenated hydrocarbon radicals having from 1 to 18 carbon atom(s) per radical, X is a radical selected from the group consisting of chlorine atoms and a radical of the formula —OR$^1$, where R$^1$ is an alkyl radical having from 1 to 8 carbon atom(s) per radical, which can be substituted by an ether oxygen atom, a is 0 or 1, with an average of from 0.01 to 1.0, b is 0, 1, 2 or 3, with an average of from 0.0 to 3.0, c is 0, 1, 2 or 3, with an average of from 0.0 to 3.0, the sum of a+b+c≦4, and is an average of from 1.5 to 4.0, and A is a radical of the formula

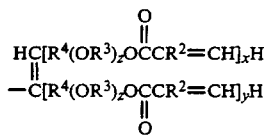

where x is 0 or 1 and y is 0 or 1, with the proviso that the sum of x+y is 1, z is 1, 2, 3 or 4, R$^2$ is selected from the group consisting of a hydrogen atom and a methyl radical, R$^3$ is a radical selected from the group consisting of the formula —CH$_2$CH$_2$—and —C(CH$_3$)HCH$_2$-—and R$_4$ is a linear or branched alkylene radical having from 1 to 6 carbon atom(s) per radical, with the proviso that the compounds contain at least one radical A per molecule.

2. The organosilicon compound containing (meth)acryloxy groups of claim 1, in which the organosilicon is a silane or organopolysiloxane.

3. The organosilicon compound containing (meth)acryloxy groups of claim 1, in which the organosilicon is a silane of the formula

 (II)

where R is a radical selected from the group consisting of monovalent hydrocarbon radicals having from 1 to 18 carbon atom(s) per radical and monovalent halogenated hydrocarbon radicals having from 1 to 18 carbon atom(s) per radical, X is a radical selected from the group consisting of a chlorine atom and a radical of the formula —OR$^1$, where R$^1$ represents an alkyl radical having from 1 to 8 carbon atom(s) per radical which can be substituted by an ether oxygen atom, d is 0, 1 or 2 and A is a radical of the formula

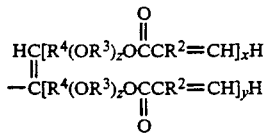

where x is 0 or 1 and y is 0 or 1, with the proviso that the sum of x+y is 1, z is 1, 2, 3 or 4, R$^2$ is selected from the group consisting of a hydrogen atom and a methyl radical, R$^3$ is selected from the group consisting of a radical of the formula —CH$_2$CH$_2$—and —C(CH$_3$)HCH$_2$—and R$^4$ is a linear or branched alkylene radical having from 1 to 6 carbon atom(s) per radical.

4. The organosilicon compound containing (meth)acryloxy groups of claim 1, in which the organosilicon is an organopolysiloxane of the formula

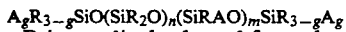 (III)

where R is a radical selected from the group consisting of monovalent hydrocarbon radicals having from 1 to 18 carbon atom(s) per radical and monovalent halogenated hydrocarbon radicals having from 1 to 18 carbon atom(s) per radical, A is a radical of the formula

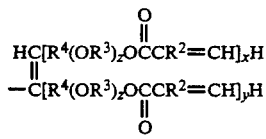

where x is 0 or 1 and y is 0 or 1, with the proviso that the sum of x+y is 1, z is 1, 2, 3 or 4, R$^2$ is selected from the group consisting of a hydrogen atom and a methyl radical, R$^3$ is selected from the group consisting of a radical of the formula —CH$_2$CH$_2$—and —C(CH$_3$)HCH$_2$—, R$^4$ is a linear or branched alkylene radical having from 1 to 6 carbon atom(s) per radical, g is 0 or 1, n is 0 or an integer of from 1 to 1500 and m is 0 or an integer of from 1 to 100, with the proviso that the organopolysiloxane contains at least one radical A per molecule.

5. The organosilicon compound containing (meth)acryloxy groups of claim 1, in which A is a radical of the formula

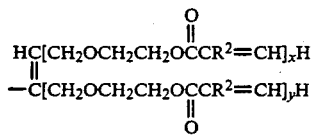

where x is 0 or 1 and y is 0 or 1, with the proviso that the sum of x+y is 1, and R$^2$ is selected from the group consisting of a hydrogen atom and a methyl radical.

6. A composition which is capable of being crosslinked by irradiation with light comprising (A) the organopolysiloxane contianing (meth)acryloxy groups of claim 1 and (B) a photosensitizer.

7. A composition which is capable of being crosslined by irradiaiton with light comprising (A) the organopolysiloxane containing (meth)acryloxy groups of claim 4 and (B) a photosensitizer.

8. A composition which is capable of being crosslinked by irradiation with light comprising (A) the organopolysiloxane containing (meth)acryloxy groups of claim 5 and (B) a photosensitizer.

9. A coating composition which is capable of being cross-linked by irradiation with light comprising (A) the organopolysiloxane containing (meth)acryloxy groups of claim 1 and (B) a photosensitizer.

* * * * *